(12) United States Patent
Provencher et al.

(10) Patent No.: US 12,318,320 B1
(45) Date of Patent: Jun. 3, 2025

(54) SHOULDER SUPPORT DEVICES AND METHODS

(71) Applicant: Proven Design Lab LLC, Dover, NH (US)

(72) Inventors: Matthew Provencher, Edwards, CO (US); Tyler Joseph Zajac, San Diego, CA (US)

(73) Assignee: Proven Design Lab LLC, Dover, NH (US)

( * ) Notice: Subject to any disclaimer, the term of this patent is extended or adjusted under 35 U.S.C. 154(b) by 0 days.

(21) Appl. No.: 18/927,300

(22) Filed: Oct. 25, 2024

Related U.S. Application Data (63) Continuation of application No. 18/664,162, filed on May 14, 2024, which is a continuation of application No. 18/491,747, filed on Oct. 20, 2023, which is a continuation-in-part of application No. 17/721,341, filed on Apr. 14, 2022, now abandoned.

(60) Provisional application No. 63/174,685, filed on Apr. 14, 2021.

(51) Int. Cl.
  *A61F 5/40* (2006.01)
  *A61F 5/01* (2006.01)
  *A61F 5/37* (2006.01)

(52) U.S. Cl.
  CPC ................ *A61F 5/0118* (2013.01)

(58) Field of Classification Search
  CPC .... A61F 5/3746; A61F 5/3723; A61F 5/3715; A61F 5/3793; A61F 5/3753; A61F 5/373; A61F 5/37; A61F 5/0118; A61F 5/013; A61F 5/40
  See application file for complete search history.

(56) References Cited

U.S. PATENT DOCUMENTS

| 5,628,725 | A  | 5/1997 | Ostergard |
| 5,857,990 | A  | 1/1999 | Maas |
| 7,785,281 | B2 | 8/2010 | Scott |

(Continued)

OTHER PUBLICATIONS

Patent assignment cover sheet and attachment for a new assignment listing Arni Thor as conveying party and Tighties, Inc. as receiving party, recorded Mar. 5, 2024 under reel: 066731 frame: 0894; 25 pages.

(Continued)

*Primary Examiner* — Camtu T Nguyen
(74) *Attorney, Agent, or Firm* — Santangelo Law Offices, P.C.

(57) ABSTRACT

Shoulder support systems and methods for treatment of the shoulder, where the ability to maintain some level of arm rotation and abduction is desired to promote positive health outcomes and ability to perform activities of daily living. Systems may comprise a vest and at least one support strap. The vest may be configured to cover an upper portion of a torso, shoulders, and at least a portion of upper arms. Pairs of sagitally mirrored anchor points may be positioned on the body and sleeves of the vest. Support straps may be attached to the anchor points. A path of the support straps may transverse the sagittal plane and spiral around an arm. Inelastic or strongly elastic cables may run a length of the support straps. Tensioning mechanisms may adjust the length of the cables to achieve the desired resistive forces for the support straps.

18 Claims, 10 Drawing Sheets

(56) References Cited

U.S. PATENT DOCUMENTS

| | | | |
|---|---|---|---|
| 7,871,388 B2* | 1/2011 | Brown | A61F 5/3746 602/19 |
| 8,007,457 B2 | 8/2011 | Taylor | |
| 8,341,772 B1 | 1/2013 | Flores | |
| 9,168,167 B2* | 10/2015 | Brown | A61F 5/026 |
| 9,226,534 B2* | 1/2016 | Puni | A41B 1/08 |
| 10,314,732 B2* | 6/2019 | Chahrour | A41D 31/18 |
| 11,622,876 B2* | 4/2023 | Matthews | A61F 5/0118 602/21 |
| 2008/0208092 A1 | 8/2008 | Sawa | |
| 2014/0174454 A1 | 6/2014 | Naef | |
| 2017/0231798 A1* | 8/2017 | Shin | A41D 31/18 2/44 |
| 2022/0031490 A1 | 2/2022 | Matthews | |
| 2022/0331141 A1 | 10/2022 | Thor et al. | |
| 2024/0058150 A1 | 2/2024 | Thor et al. | |

OTHER PUBLICATIONS

Patent assignment cover sheet and attachment for a new assignment listing Tighties, Inc. as conveying party and Arni Thor as receiving party, recorded Feb. 28, 2024 under reel: 066703 frame: 0146; 25 pages.

Patent assignment cover sheet and attachment for a corrected assignment listing Arni Thor as conveying party and Tighties, Inc. as receiving party, recorded Mar. 13, 2024 under reel: 066794 frame 0464; 27 pages.

U.S. Appl. No. 63/174,685, filed Apr. 14, 2021, first named inventor: Matthew T. Provencher.

U.S. Appl. No. 17/721,341, filed Apr. 14, 2022, first named inventor: Arni Thor, Office Action dated Jul. 18, 2023, 5 pages.

U.S. Appl. No. 17/721,341, filed Apr. 14, 2022, first named inventor: Arni Thor, Notice of Allowance dated Jan. 22, 2024, 10 pages.

U.S. Appl. No. 18/491,747, filed Oct. 20, 2023, first named inventor: Arni Thor.

U.S. Appl. No. 18/664,162, filed May 14, 2024, first named inventor: Matthew Provencher.

U.S. Appl. No. 17/721,341, filed Apr. 14, 2022, first named inventor: Arni Thor, Notice of Allowance dated May 31, 2024, 9 pages.

U.S. Appl. No. 18/491,747, filed Oct. 20, 2023, first named inventor: Arni Thor. Office Action dated Dec. 9, 2024, 6 pages.

U.S. Appl. No. 18/664,162, filed May 14, 2024, first named inventor: Matthew Provencher. Notice of Abandonment dated Dec. 12, 2024, 2 pages.

U.S. Appl. No. 17/721,341, filed Apr. 14, 2022, first named inventor: Arni Thor. Notice of Abandonment dated Sep. 11, 2024, 1 page.

* cited by examiner

SHOULDER SUPPORT DEVICES AND METHODS

CROSS-REFERENCE TO RELATED APPLICATIONS

This patent application is a continuation of U.S. application Ser. No. 18/664,162 filed on May 14, 2024 which is a continuation of U.S. application Ser. No. 18/491,747 filed Oct. 20, 2023 which is a continuation-in-part of U.S. application Ser. No. 17/721,341 filed Apr. 14, 2022 which claims the benefit of and priority to U.S. Provisional Patent Application Ser. No. 63/174,685, titled "SHOULDER SUPPORT DEVICES AND METHODS OF USING THE SAME," filed Apr. 14, 2021, each said application is hereby incorporated herein by reference in its entirety.

BACKGROUND

Field of the Invention

The invention relates generally to systems and methods of restricting movement of body parts, and, in particular, to a rotation & abduction device for shoulder control and methods of its use. The invention also relates to control of adduction, internal rotation, external rotation, flexion, and extension of the shoulder and elbow.

Scope of the Prior Art

To promote healing after a shoulder surgery or injury, the shoulder movement is often restricted. Many solutions to restrict shoulder movement have been put forth in the prior art. Some of these include:

"Gun slinger" and "Airplane" type braces: These braces restrict not just the shoulder but the entire arm, including the elbow and wrist. Excessive immobilization of the elbow and wrist can cause swelling, poor lymph drainage, reduced health outcomes, and reduced ability to perform activities of daily living (ADL). Women have historically found such braces to be extremely uncomfortable around the breast and shoulders. Furthermore, most patients find them challenging to put on and properly adjust.

Traditional slings: These braces are intended purely for immobilization. However, it has been shown that early mobilization can lead to improved health outcomes and improved ability to perform ADLs. Allowing for some early but safe muscle activation is therefore much needed.

Post operatively patients are required to exercise with a physical therapist or athletic trainer to gain back prior strength. Patients are often non-compliant with therapy and do not like having to spend hours in a therapy room. Garments that provide resistance training or proprioception support, as well as movement control, are therefore much needed to bypass long sessions of physical therapy. Such a garment would include support straps that are easily attached, adjustable in tension, and adjustable in resistance by a physical therapist. Wearing the garment passively trains the patient during everyday activities.

Lastly, most shoulder slings are intended for all different types of shoulder injuries and surgeries. However, to optimally treat each patient, it is important to understand which movements are safe for a patient, and to only allow for those movements. Having a dozing system of some sort to control these different movements with protocols behind each indication is therefore much needed.

SUMMARY

The present disclosure satisfies the foregoing needs by providing, inter alia, shoulder support systems for addressing each of the foregoing desirable traits, as well as methods of their use.

One aspect of the present disclosure is directed at a shoulder support system that is comfortable to wear. Preferably, the elbow and wrist remain completely free while the shoulder is controlled in the appropriate manner. This prevents any interference with most ADLs.

Another aspect of the present disclosure is directed at a shoulder support system that can provide controlled and adjustable restriction of one or more of internal rotation, external rotation, abduction, adduction, flexion, or extension, as well as movement enhancements, proprioception, posture control, and muscle training, making the process of regaining lost strength easier and more effective.

Yet another aspect of the present disclosure is directed at a method to support the shoulder. The method provides controlled and adjustable restriction of one or more of internal rotation, external rotation, abduction, adduction, flexion, or extension, as well as movement enhancements, proprioception, posture control and muscle training.

BRIEF DESCRIPTION OF THE DRAWINGS

The foregoing summary, as well as the following detailed description of preferred variations of the invention, will be better understood when read in conjunction with the appended drawings. For the purpose of illustrating the invention, there is shown in the drawings variations that are presently preferred. It should be understood, however, that the invention is not limited to the precise arrangements shown. In the drawings, where:

FIG. 1B is a back view of the vest of FIG. 1a.

FIG. 2b is an inside view of the support strap of FIG. 2a.

FIG. 3b is an inside view of the support strap of FIG. 3a.

FIG. 6b is a back view of the shoulder support system of FIG. 6a.

FIG. 7b is a back view of the vest of FIG. 7a.

FIG. 8b is a back view of the shoulder support system of FIG. 8a.

DETAILED DESCRIPTION

Implementations of the present technology will now be described in detail with reference to the drawings, which are provided as illustrative examples so as to enable those skilled in the art to practice the technology. Notably, the figures and examples below are not meant to limit the scope of the present disclosure to any single implementation or implementations, but other implementations are possible by way of interchange of, substitution of, or combination with some or all of the described or illustrated elements. Wherever convenient, the same reference numbers will be used throughout the drawings to refer to same or like parts.

Moreover, while embodiments described herein are primarily discussed in the context of shoulder systems and methods for the treatment of the shoulder, as well as for muscular training, it will be recognized by those of ordinary skill that the present disclosure is not so limited. In fact, the principles of the present disclosure described herein may be readily applied to the treatment of other parts of the human anatomy. For example, many common knee or elbow injuries require the partial immobilization of a joint. Accordingly, the principles described herein may be readily adapted for use on the arm, elbow, ankle, etc., where movement, whether in extension, flexion, adduction, abduction, internal rotation, or external rotation, may need to be constrained in order to facilitate recovery from, for example, an injury or other medical condition, as well as to reduce pain or to help provide bio feedback to train muscles in order to prevent future injuries.

In the present specification, an implementation showing a singular component should not be considered limiting; rather, the disclosure is intended to encompass other implementations including a plurality of the same component, and vice-versa, unless explicitly stated otherwise herein. Further, the present disclosure encompasses present and future known equivalents to the components referred to herein by way of illustration.

It will be recognized that while certain aspects of the technology are described in terms of a specific sequence of steps of a method, these descriptions are only illustrative of the broader methods of the disclosure and may be modified as required by the particular application. Certain steps may be rendered unnecessary or optional under certain circumstances. Additionally, certain steps or functionality may be added to the disclosed implementations, or the order of performance of two or more steps permuted. All such variations are considered to be encompassed within the disclosure disclosed and claimed herein.

Figure 1A:
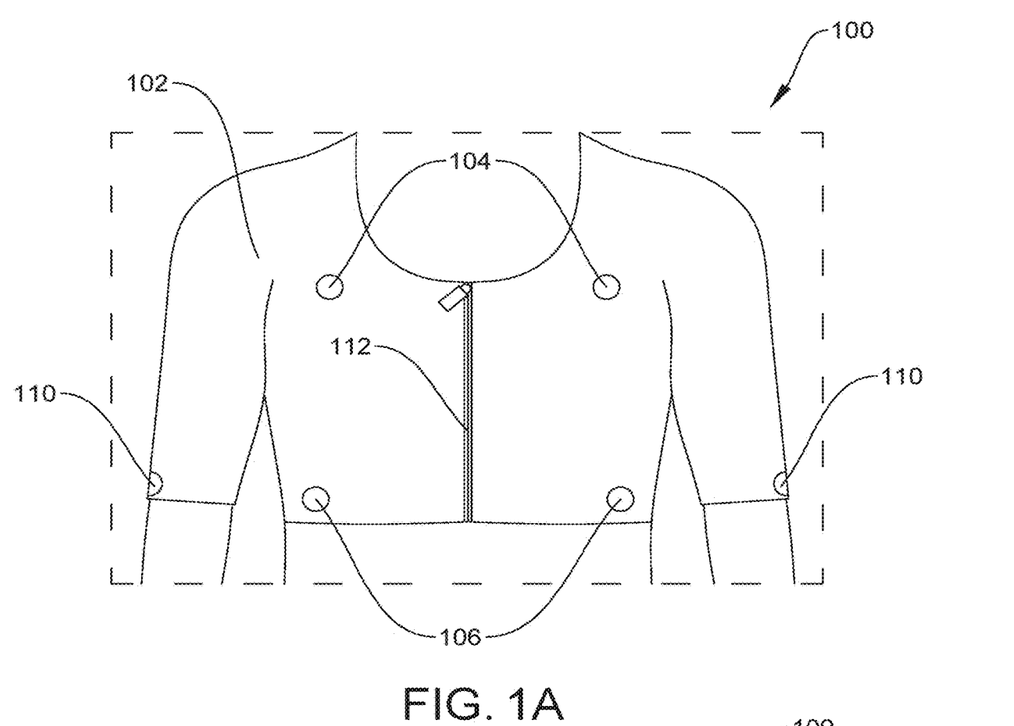
FIG. 1a is a front view of a vest, according to one embodiment.
Figure 1B:
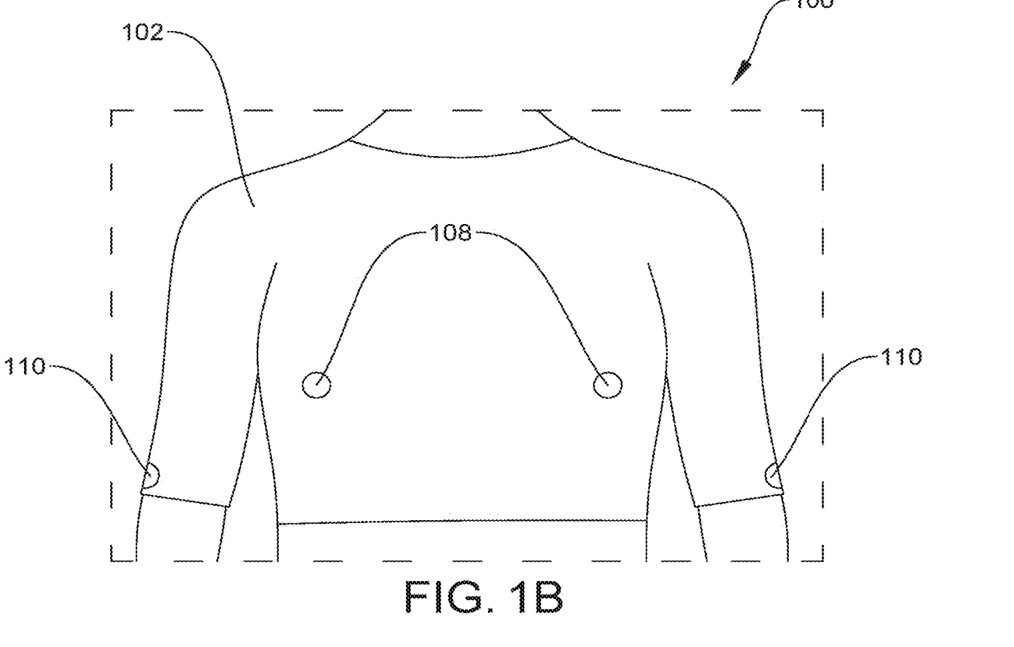

Referring now to FIGS. 1a-1b, one exemplary vest 100 is illustrated and described in detail below. FIG. 1a shows the vest 100, on a wearer, from a front view and FIG. 1b shows the vest 100, on a wearer, from a back view.

The vest 100 may be comprised of a weakly elastic portion 102 that weakly resists stretching under tensile forces, such as spandex, and is designed to fit snugly against the wearer's body. Portions of the vest 100 that require extra stiffness, for example around anchor points, may be comprised of a material that strongly resists stretching under tensile forces, such as nylon. These strongly elastic portions may be disposed within the weakly elastic portion 102 via integration through sewing, adhesives, and the like. Alternatively, the strongly elastic portions may be created by gluing a polyurethane film or silicone onto the weakly elastic portion 102 to create inelastic areas and/or to impact the level of stretch where extra stiffness is required. Yet alternatively, the strongly elastic portions may be may of an inelastic material.

The vest 100 may cover an upper portion of a torso, shoulders, and at least a portion of upper arms. Preferably, the sleeves of the vest 100 terminate above a wearer's elbows.

At least one front pair of anchor points may be positioned on the front portion of the vest 100. Here, a first pair of anchor points 104 is positioned on the front portion of the vest 100. Preferably, the anchor points 104 are mirrored around the sagittal plane and sit over a wearer's pectorals. A second pair of anchor points 106 is positioned on the front portion of the vest 100 below the first pair of anchor points 104. Preferably, the anchor points 106 are mirrored around the sagittal plane and sit over a wearer's obliques or abdominal muscles.

At least one back pair of anchor points may be positioned on the back portion of the vest 100. Here, a third pair of anchor points 108 is positioned on the back portion of the vest 100. Preferably, the anchor points 108 are mirrored around the sagittal plane and sit over a wearer's latissimus muscles.

At least one distal pair of anchor points may be positioned on the distal portion of the sleeves of the vest 100. Here, a fourth pair of anchor points 110 is positioned distally on the sleeves of the vest 100. Preferably, the anchor points 110 are mirrored around the sagittal plane and sit over a wearer's triceps.

The anchor points may each be one part of any two part fastening mechanism such as one part of a hook and loop fastener, one part of a snap fastener, or one part of a zipper. Preferably, the anchor points are integrated into vest 100. Alternatively, the anchor points are attached to the vest 100 through common physical or chemical means, including, but not limited to, sewing, adhesives, binding, and the like. The anchor points are configured to receive an end of a support strap as will be later discussed.

A closure mechanism 112 on the vest 101, such as a zipper, improves the vest's ease of use. The wearer may put on the vest 101 using only one of his or her arms.

Figure 2A:
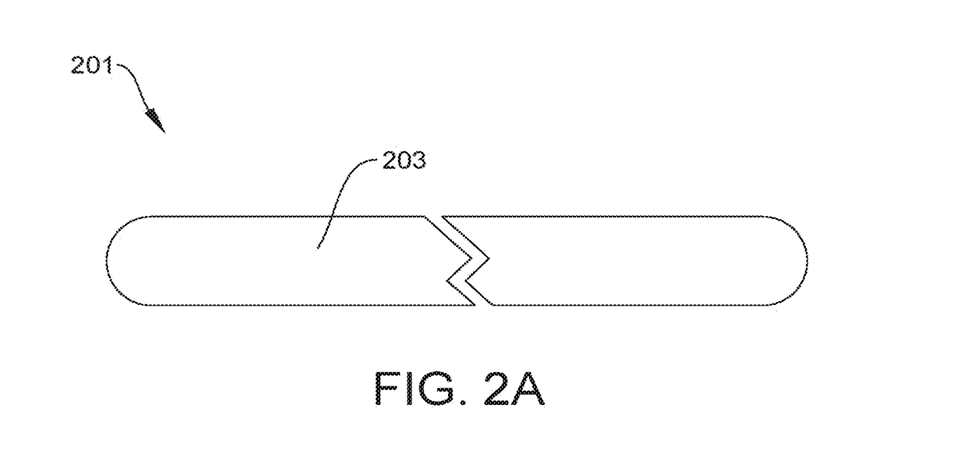
FIG. 2a is an outside view of a support strap, according to one embodiment.
Figure 2B:
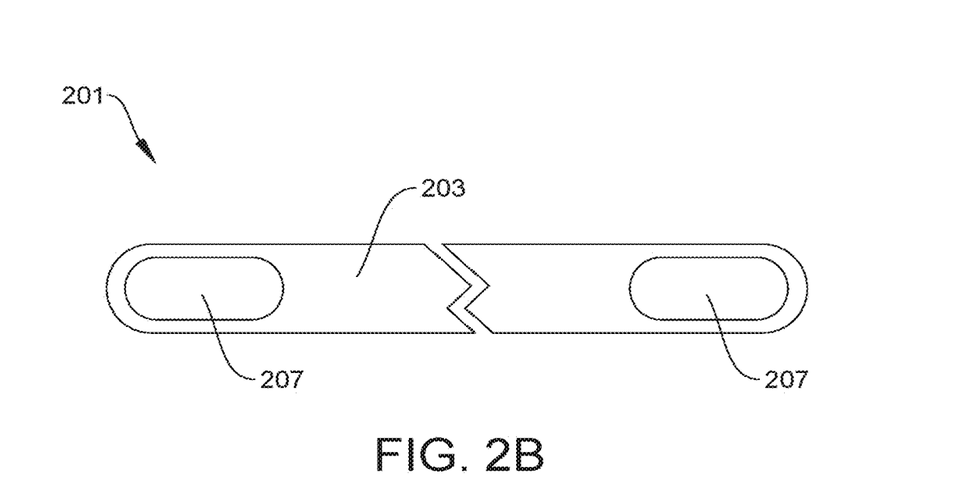

Referring now to FIGS. 2a-2b, one exemplary support strap 201 is illustrated and described in detail below. FIG. 2a shows the strap 201 from an outside view and FIG. 2b shows the strap 201 from an inside view. The strap 201 is not drawn to scale and the break in the strap 201 is indicative of the strap's variable length.

The strap body 203 may be a flat stretch of an elastic material or fabric, for example, but not limited to, a flat stretch of spandex, rubber, and the like.

Attachment areas 207 may be positioned on ends of the strap 201. Attachment areas 207 may each be one part of any two-part fastening mechanism such as one part of a hook and loop fastener, one part of a snap fastener, or one part of a zipper. Anchor points and attachment areas should use corresponding fastening mechanisms. For example, anchor points may be a hook portion of a hook and loop fastener, and the attachment areas 207 may be a loop portion of a hook and loop fastener. Attachment areas 207 allow the ends of the strap 201 to be attached to anchor points.

Figure 3A:
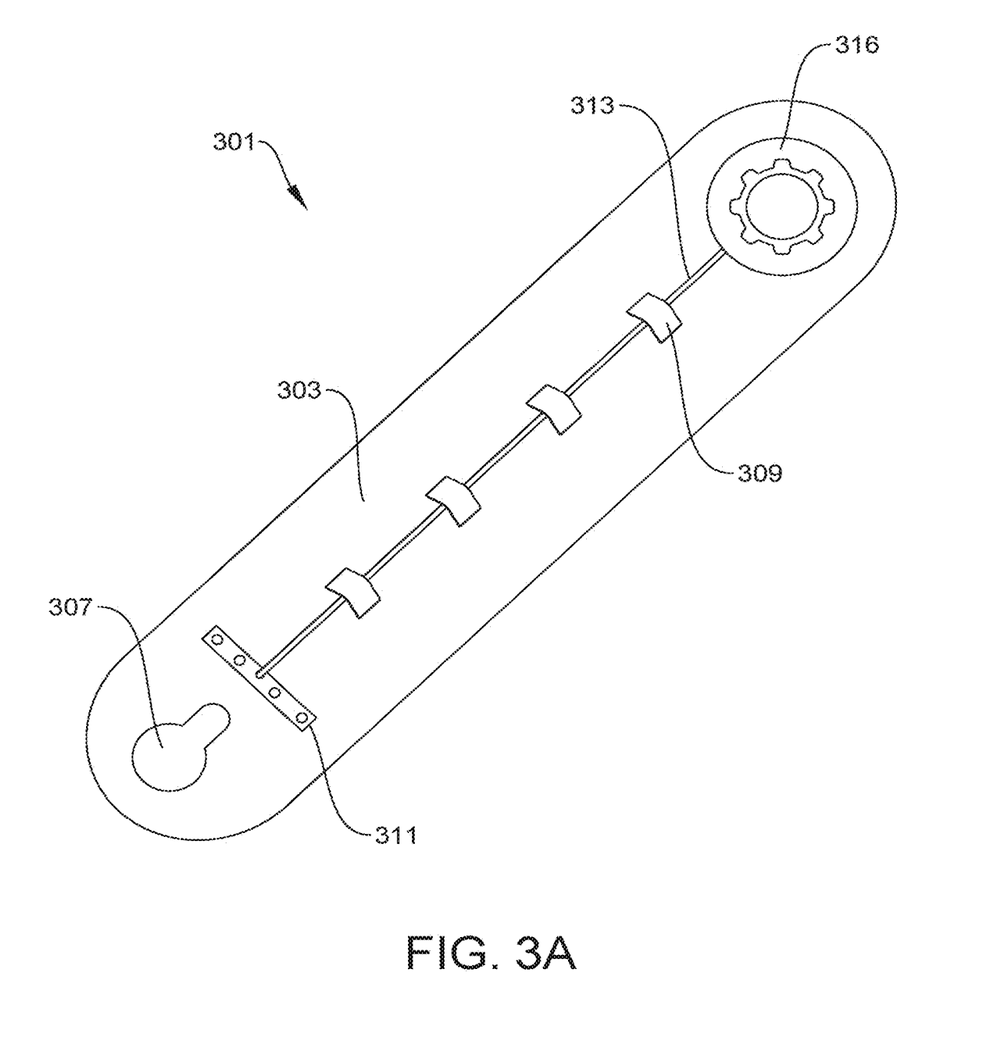
FIG. 3a is an outside view of a support strap, according to another embodiment.
Figure 3B:
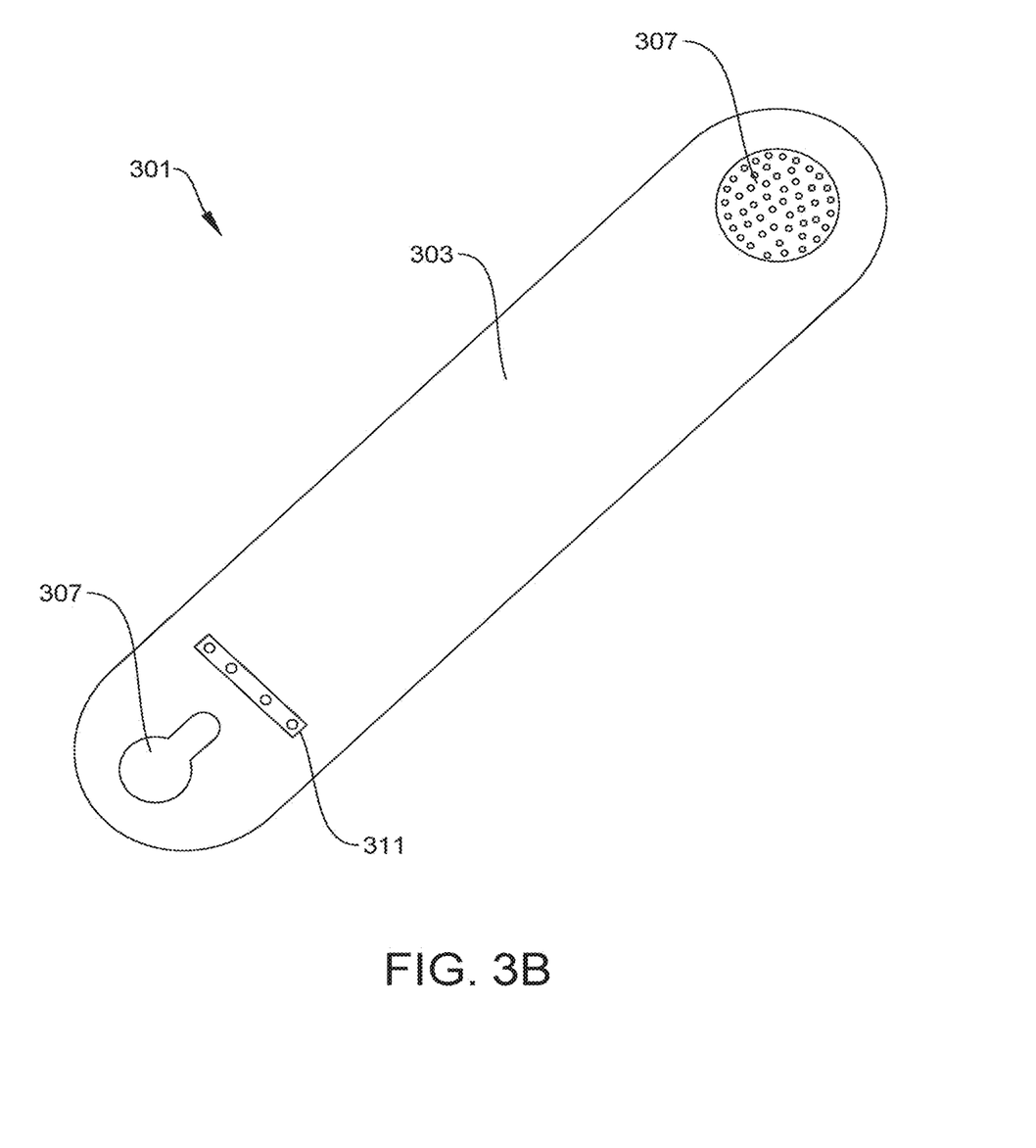

Referring now to FIGS. 3a-3b, one exemplary adjustable support strap 301 is illustrated and described in detail below. FIG. 3a shows the strap 301 from an outside view and FIG. 3b shows the strap 301 from an inside view. The strap 301 is not drawn to scale and the strap 301 has variable length.

The strap body 303 may be a flat stretch of an elastic material or fabric, for example, but not limited to, a flat stretch of spandex, rubber, and the like.

Attachment areas 307 may be positioned on ends of the strap 301. Attachment areas 307 may each be one part of any two-part fastening mechanism such as one part of a hook and loop fastener, one part of a snap fastener, or one part of a zipper. Here, one attachment area 307 is a loop portion of a hook and loop fastener and the other attachment area 307 is a keyhole.

The strap 301 may have an inner surface and an outer surface, where the inner surface of the strap faces an outer surface of the vest when attached to the vest.

The strap 301 may further comprise a cable anchor 311. The cable anchor 311 is used to secure one end of a cable 313 to the strap body 303. Preferably, the cable anchor 311 is made of two thin metal plates, on opposite sides of the strap body 303, coupled together to the strap body 303 using rivets. There is a small opening on the top metal plate to hold one end of a cable 313. Alternatively, the cable anchor 311 may be any part or arrangement of parts attached to the strap body 303 that can hold an end of a cable 313. The cable anchor 311 may contact a large surface area of the strap body 303 to evenly distribute any tensive forces of the cable 313.

The strap 301 may further comprise at least one guide segment 309. Preferably, there are several guide segments 309 between the cable anchor 311 and the tensioning mechanism 316. The guide segments 309 are semi-tubular portions of the strap body 303 that extend out from the strap body 303. Alternatively, the guide segment 309 may be a channel in the strap body 303 that runs along the length of the strap body 303, with openings, for the cable 313, near the cable anchor 311 and the tensioning mechanism 316.

The tensioning mechanism 316 may be positioned on the strap body 303 distal to the cable anchor 311 and may be attached to the strap body 303 through common physical or chemical means such as sewing, screws, adhesives, and the like. Preferably, the tensioning mechanism is a BOA rotary dial. The BOA rotary dial can change the length of a cable 313. Alternatively, the tensioning mechanism 316 may be any mechanism that can vary the length of the cable 313, such as hook and loop straps, button loop straps, and the like.

A cable 313 may run through the guide segments 309. The first end of the cable 313 may be integrated into a tensioning mechanism 316 and the second end of the cable 313 may be secured to the cable anchor 311. The length of the cable 313 may be adjusted using the tensioning mechanism 316.

Preferably, the cable 313 is made of an inelastic material, such as steel. In this embodiment, tightening the cable 313 reduces the maximum stretch distance of the strap body 303, where the strap body 303 cannot be stretched much longer than the length of the cable 313 that runs through it. Alternatively, the cable 313 is made of a strongly elastic material that strongly resists stretching under tensile forces, such as nylon. In this embodiment, tightening the cable 313 increases the strap body's 303 resistance to stretching.

The strap 301 may be removable and interchangeable, wherein a wearer can swap out a first strap 301 for a second strap that may have different tensive properties. For example, a wearer can swap to a thicker second strap. The increased thickness of the strap would increase the straps' resistance to being stretched so a wearer using the new strap would not have to rotate their arm as far and/or tighten the tensioning mechanism 316 as much to achieve the same reactive torque. Thus, the strap 301 can be customized to achieve the desired reaction.

Figure 4A:
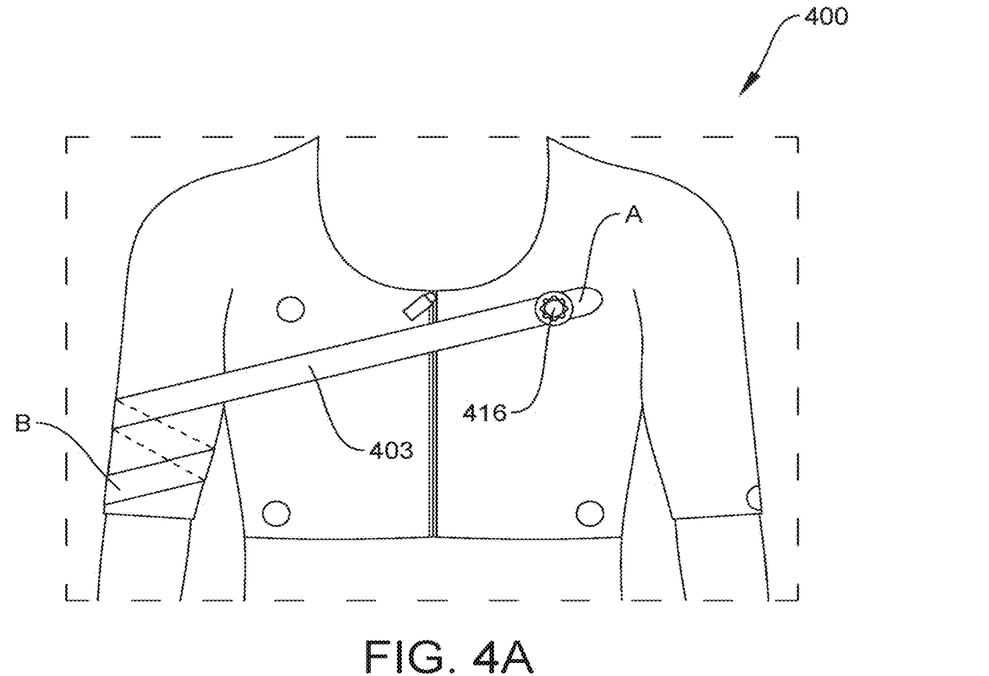
FIG. 4a is a front view of a shoulder support system, with a first strapping configuration, according to one embodiment.
Figure 4B:
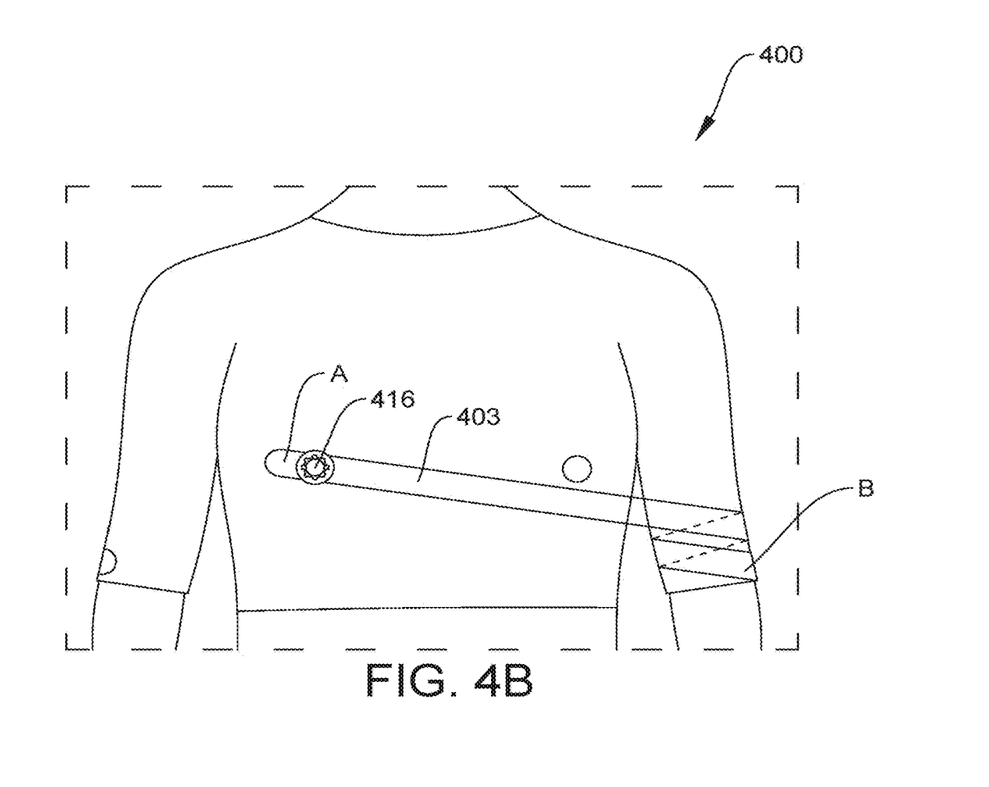
FIG. 4b is a back view of a shoulder support system, with a second strapping configuration, according to another embodiment.

Referring now to FIGS. 4a-4b, one exemplary shoulder support system strap 400 is illustrated and described in detail below. FIG. 4a shows the system 400, with a first strap configuration, from a front view and FIG. 4b shows the system 400, with a second strap configuration, from a back view. The system 400 may be comprised of the vest of FIGS. I a-1 b and the adjustable support strap of FIGS. 3a-3b. These strap configurations may be used to restrict and/or limit shoulder movement to promote healing after a shoulder surgery or injury.

Figure 5A:
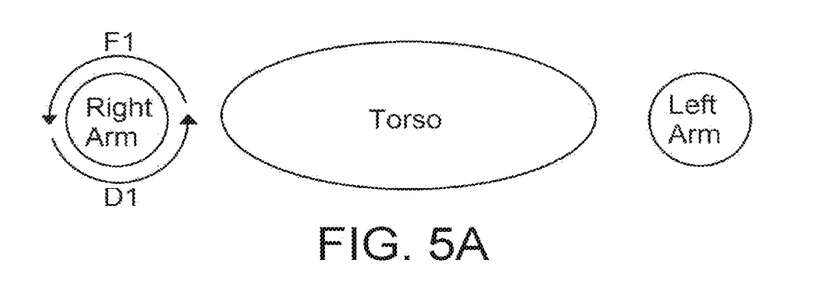
FIGS. 5a-5c show some of the forces imparted onto a wearer's arm by the shoulder support systems of this disclosure.

In FIG. 4a, the strap 403 starts at point A, where its first end is attached to one of the anchor points in the first pair of anchor points. The strap 403 continues across the wearer's chest and spirals clockwise down the wearer's arm. The strap 403 ends at point B, where its second end is attached to one of the anchor points in the fourth pair of anchor points. FIG. Sa shows how, for this first strap configuration, when stretched during external rotation of the arm, or during tensioning with the tensioning mechanism 416, the strap's 403 resistance to stretching imparts an inwards torque F1 to the arm, inducing internal rotation in direction D1.

Figure 5B:
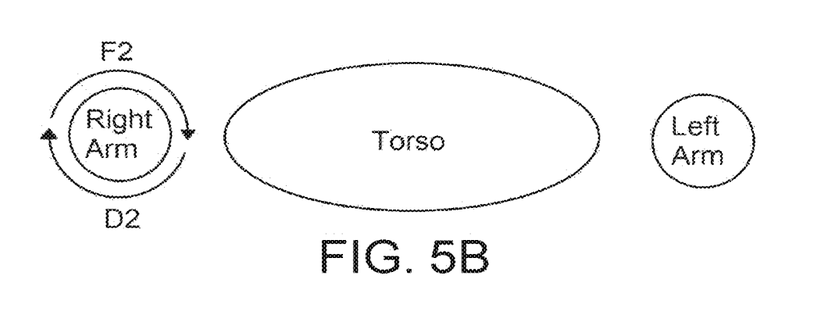

In FIG. 4b, the strap 403 starts at point A, where its first end is attached to one of the anchor points in the third pair of anchor points. The strap 403 continues across the wearer's back and spirals counterclockwise down the wearer's arm. The strap 403 ends at point B, where its second end is attached to one of the anchor points in the fourth pair of anchor points. FIG. 5b shows how, for this second strap configuration, when stretched during internal rotation of the arm, or during tensioning with the tensioning mechanism 416, the strap's 403 resistance to stretching imparts an outwards torque F2 to the arm, inducing external rotation in direction D2.

A wearer can choose which rotational forces his or her arm is subjected to depending on where he or she attaches the first end of the strap 403. Attaching the strap 403 to a front anchor point on the front of the vest will result in a clockwise spiral around the wearer's arm and resistance to external rotation of the arm while attaching the strap 403 to a back anchor point on the back of the vest will result in a counterclockwise spiral around the wearer's arm and resistance to internal rotation of the arm.

Figure 5C:
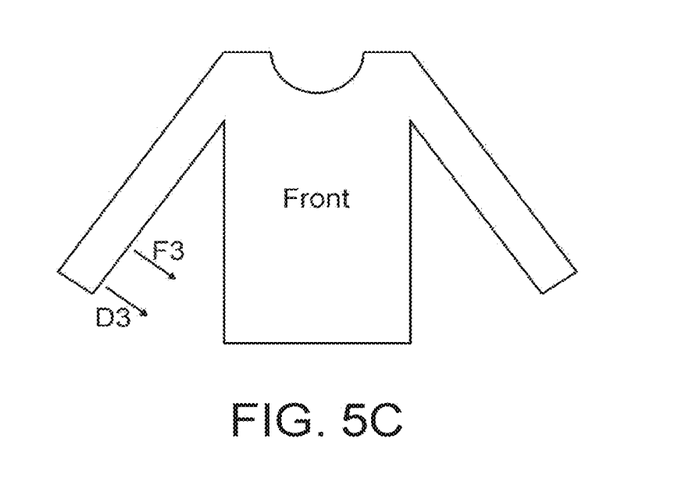

FIG. 5c shows how, for both the first and second strap configurations, when stretched during arm abduction, or during tensioning with the tensioning mechanism, the strap's 403 resistance to stretching imparts an adduction force F3 to the arm, inducing arm adduction in direction D3.

A wearer can adjust the direction of the adduction force depending on where he or she attaches the first end of the strap 403. Attaching the strap 403 on a higher anchor point on the body angles the direction of the adduction force upwards while attaching the strap 403 on a lower anchor point on the body angles the direction of the adduction force downwards. Various anchor points on the body may also be chosen to adjust the path of the strap. For example, a strap 404 can start on a higher or lower anchor point to avoid crossing over, and thus compressing, a portion of the body that is bruised.

The path of the strap 403 across the wearer's chest or back, traversing the sagittal plane, confers several advantages over straps that do not transverse the sagittal plane. First, the increased span of the strap 403 results in a decreased spring constant in the strap 403, allowing for increased stretch distances before facing a desired resistance. This, in turn, allows a larger range of motion for cases where such mobility would benefit health outcomes. Second, the increased span of the strap 403 results in a larger contact area between the vest and the strap 403, spreading out the compressive forces imparted onto the wearer by the strap 403. This, in turn, allows for a more comfortable fitting vest.

Figure 6A:
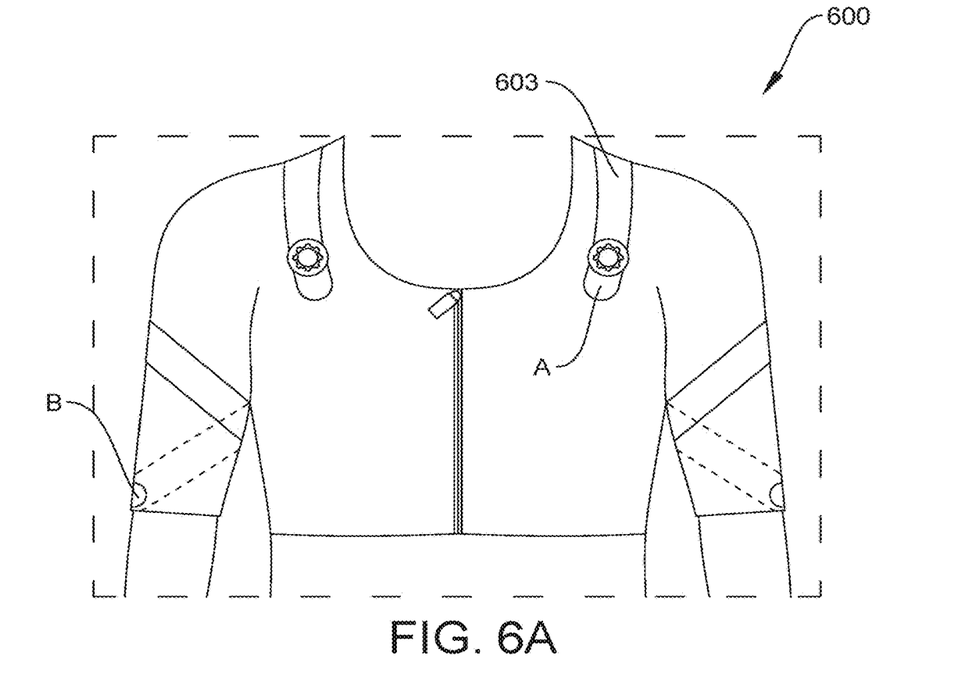
FIG. 6a is a front view of a shoulder support system, with a third strapping configuration, according to another embodiment.
Figure 6B:
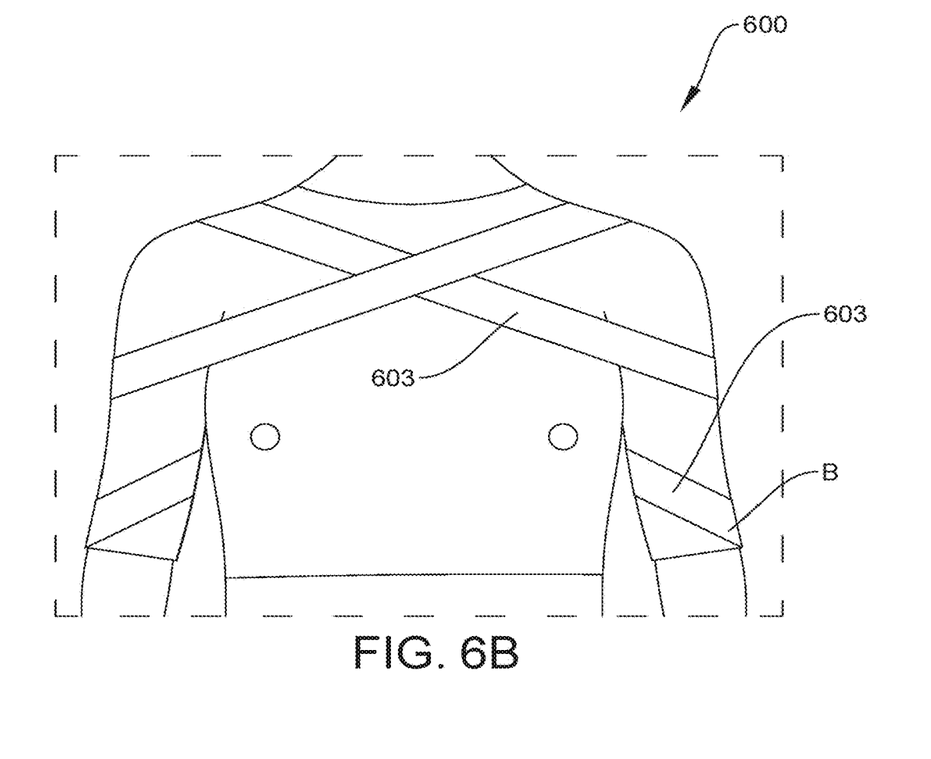

Referring now to FIGS. 6a-6b, one exemplary shoulder support system 600 is illustrated and described in detail below. FIG. 6a shows the system 600, with a third strap configuration, from a front view and FIG. 6b shows the system 600, with a third strap configuration, from a back view. The system 600 may be comprised of the vest of FIGS. 1a-1b and two of the adjustable support straps of FIGS. 3a-3b. This strap configuration may be used for passive muscle training and posture control, for example, to prepare a patient for surgery and to assist in regaining strength and proper posture after surgery.

In FIGS. 6a-6b, the strap 603 starts at point A, where its first end is attached to one of the anchor points in the first pair of anchor points. The strap 603 continues upwards around the trapezius muscles, across the back, and spirals down the wearer's arm. The strap 603 ends at point B, where its second end is attached to one of the anchor points in the fourth pair of anchor points. Here, a second strap mirrors the path of the first strap 603, wherein both straps can be adjusted to apply equal forces to opposite sides of a wearer's body. Such mirroring is possible due to the mirrored position of the anchor points on the vest.

Figure 7A:
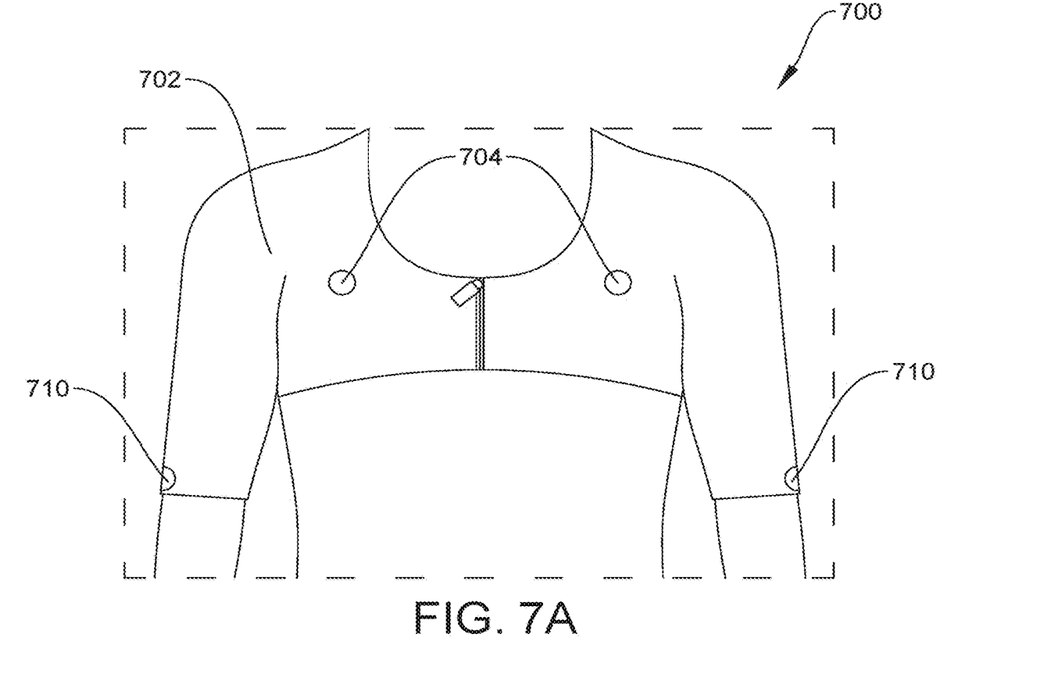
FIG. 7a is a front view of a vest, according to another embodiment.
Figure 7B:
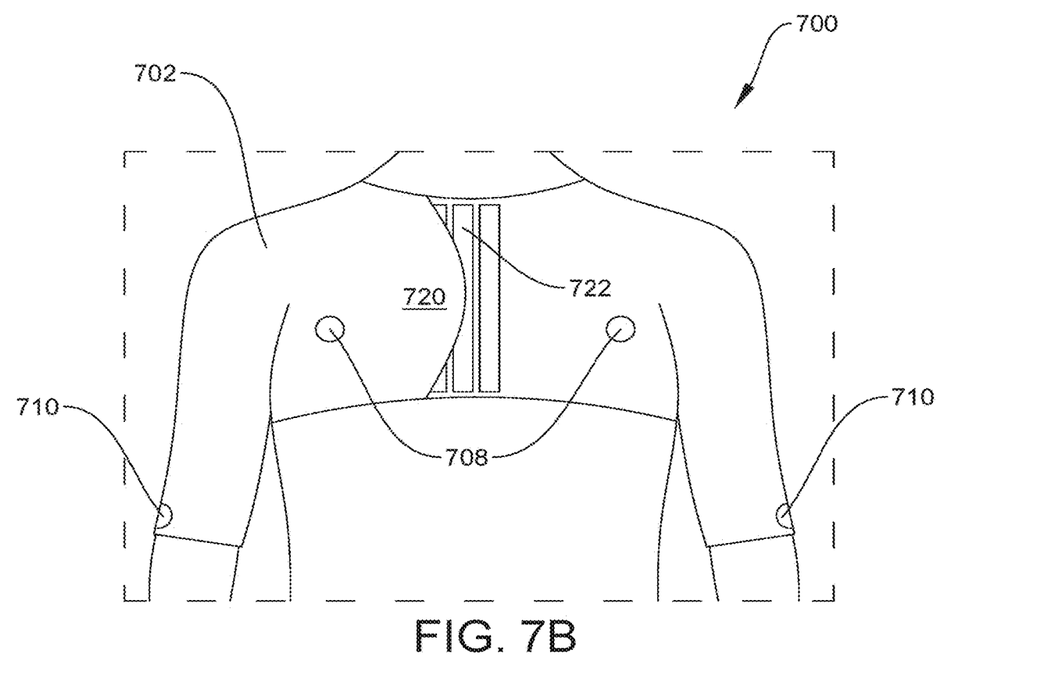

Referring now to FIGS. 7a-7b, one exemplary vest 700 is illustrated and described in detail below. FIG. 7a shows the vest 700, on a wearer, from a front view and FIG. 7b shows the vest 700, on a wearer, from a back view.

The vest 700 may be comprised of a weakly elastic portion 702 that weakly resists stretching under tensile forces, such as spandex, and is designed to fit snugly against the wearer's body. Portions of the vest 700 that require extra stiffness, for example, around anchor points, may be comprised of a material that strongly resists stretching under tensile forces, such as nylon. These strongly elastic portions may be disposed within the weakly elastic portion 702 via integration through sewing, adhesives, and the like. Alternatively, the strongly elastic portions may be created by gluing a polyurethane film or silicone onto the weakly elastic portion 702 to create inelastic areas and/or to impact the level of stretch where extra stiffness is required. Yet alternatively, the strongly elastic portions may be may of an inelastic material.

The vest 700 may cover an upper portion of a torso, shoulders, and at least a portion of upper arms. Preferably, the sleeves of the vest 700 terminate above a wearer's elbows.

At least one front pair of anchor points may be positioned on the front portion of the vest 700. Here, a first pair of anchor points 704 is positioned on the front portion of the vest 700. Preferably, the anchor points 704 are mirrored around the sagittal plane and sit over a wearer's pectorals.

At least one back pair of anchor points may be positioned on the back portion of the vest 700. Here, a second pair of anchor points 708 is positioned on the back portion of the vest 700. Preferably, the anchor points 708 are mirrored around the sagittal plane and sit near a wearer's shoulder blades.

At least one distal pair of anchor points may be positioned on the distal portion of the sleeves of the vest 700. Here, a third pair of anchor points 710 is positioned distally on the sleeves of the vest 700. Preferably, the anchor points 710 are mirrored around the sagittal plane and sit over a wearer's triceps.

The anchor points may each be one part of any two part fastening mechanism such as one part of a hook and loop fastener, one part of a snap fastener, or one part of a zipper. Preferably, the anchor points are integrated into vest 700. Alternatively, the anchor points are attached to the vest 700 through common physical or chemical means, including, but not limited to, sewing, adhesives, binding, and the like. The anchor points are configured to receive an end of a support strap as will be later discussed.

A closure mechanism 712 on the vest 700, such as a zipper, improves the vest's ease of use. The wearer may put on the vest 700 using only one of his or her arms.

An adjustment mechanism on the vest 700, such as a flap with hooks 720 and a series of loop portions 722, allows the length of the back portion of the vest 700 to be adjusted to accommodate different patients.

Figure 8A:
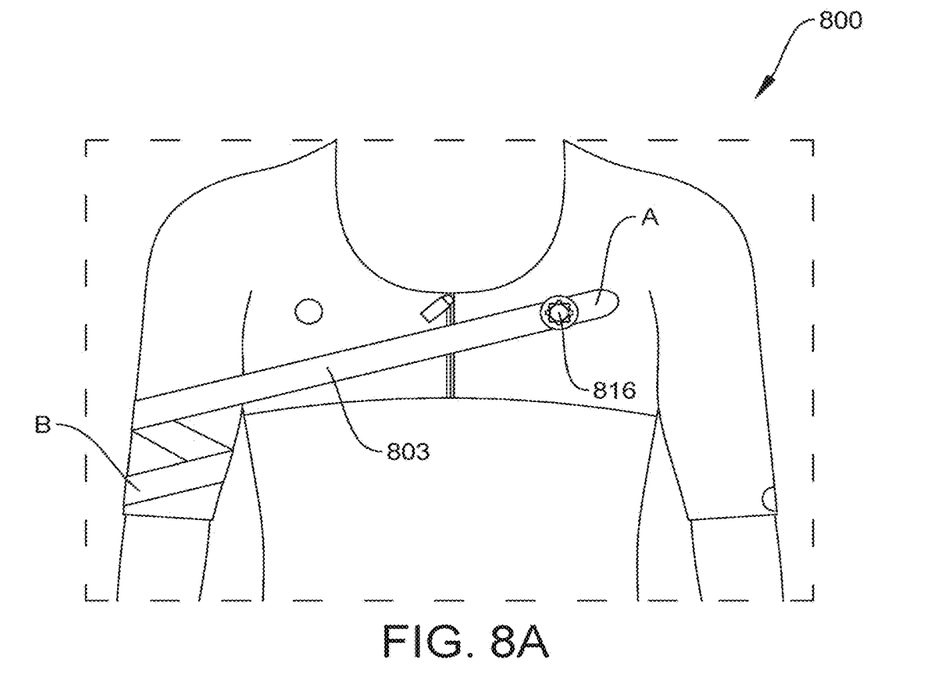
FIG. 8a is a front view of a shoulder support system, with a third strapping configuration, according to another embodiment.
Figure 8B:
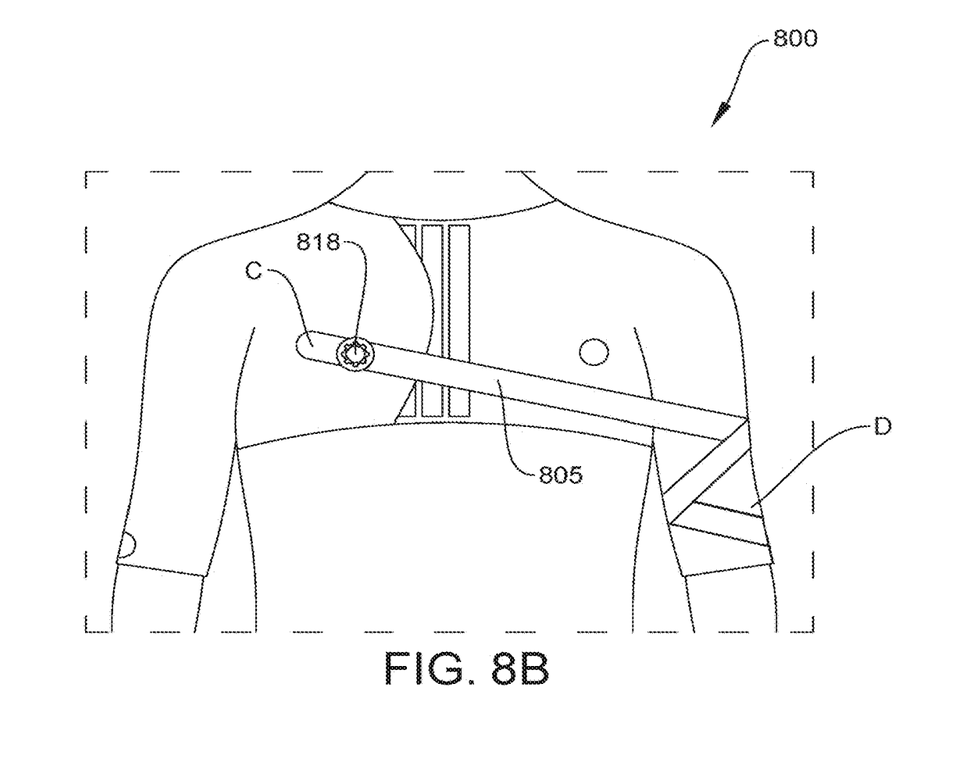

Referring now to FIGS. 8a-8b, one exemplary shoulder support system strap 800 is illustrated and described in detail below. FIG. 8a shows the system 800, with a fourth strap configuration, from a front view and FIG. 8b shows the system 800, with the fourth strap configuration, from a back view. The system 800 may be comprised of the vest of FIGS. 7a-7b and the adjustable support strap of FIGS. 3a-3b. These strap configurations may be used to restrict and/or limit shoulder movement to promote healing after a shoulder surgery or injury.

In FIG. 8a, the first strap 803 starts at point A, where its first end is attached to one of the anchor points in the first pair of anchor points. The first strap 803 continues across the wearer's chest and spirals clockwise down the wearer's arm. The first strap 803 ends at point B, where its second end is attached to one of the anchor points in the third pair of anchor points. FIG. 5a shows how, for this fourth strap configuration, when stretched during external rotation of the arm, or during tensioning with the tensioning mechanism 816, the first strap's 803 resistance to stretching imparts an inwards torque F1 to the arm, inducing internal rotation in direction DI.

In FIG. 8b, the second strap 805 starts at point A, where its first end is attached to one of the anchor points in the second pair of anchor points. The second strap 805 continues across the wearer's back and spirals counterclockwise down the wearer's arm. The strap 805 ends at point B, where its second end is attached to one of the anchor points in the third pair of anchor points. FIG. 5b shows how, for this fourth strap configuration, when stretched during internal rotation of the arm, or during tensioning with the tensioning mechanism 818, the second strap's 805 resistance to stretching imparts an outwards torque F2 to the arm, inducing external rotation in direction D2.

Attaching the first strap 803 and second strap 805 to the vest, where the two straps spiral in opposite directions around the same arm, results in a system 800 that offers both resistance to external rotation and resistance to internal rotation of the upper arm.

FIG. 5c shows how, for this fourth configuration, when stretched during arm abduction, or during tensioning with the tensioning mechanisms, the straps' resistance to stretching imparts an adduction force F3 to the arm, inducing arm adduction in direction D3.

Figure 9:
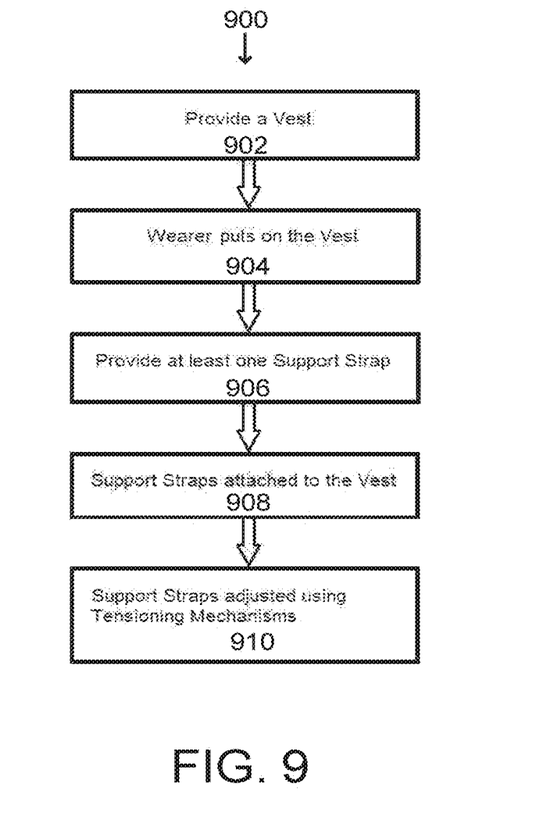
FIG. 9 is a flowchart of the steps of a method of supporting a shoulder, according to one embodiment.

Referring now to FIGS. 8a-8b, one exemplary method 900 of supporting a shoulder is illustrated and described in detail below.

The method starts at block 902. A vest is provided to the wearer. Preferably, the provided vest may be the vest of FIGS. 1a-1b or the vest of FIGS. 7a-7b. Alternatively, the provided vest may be any vest configured to cover an upper portion of a torso, shoulders, and at least a portion of upper arms, where at least one front pair of sagittally mirrored anchor points is positioned on a front portion of the vest, at least one back pair of sagitally mirrored anchor points is positioned on a back portion of the vest, and at least one distal pair of sagitally mirrored anchor points is positioned on a distal portion of the sleeves of the vest.

The method proceeds to block 904. The vest is put on by the wearer.

The method proceeds to block 906. At least one support strap is provided. Preferably, the support strap may be the support strap of FIGS. 2a-2b or the adjustable support strap of FIGS. 3a-3b. Alternatively, the support strap may be any support strap with attachment areas configured to receive an anchor point.

The method proceeds to block 908. The support straps are attached to the vest, where the first end of each support strap attaches to one of the anchor points on the body of the vest, the second end of each support strap attaches to one of the anchor points on the sleeve of the vest, the path of each support strap transverses the sagittal plane, and the path of each support strap spirals around an arm.

The method ends at block 910. The support straps may be adjusted using tensioning mechanisms.

While specific shoulder support systems and methods been contemplated, it would be readily appreciated by those in the field that the novel vest and support strap configurations, individually, or in any combination, may be applied to brace or support other parts of the body.

We claim:

1. A shoulder support system comprising:
   a vest with a pair of sleeves configured to cover an upper portion of a torso, shoulders, and at least a portion of upper arms, wherein
      an anterior pair of sagittally mirrored anchor points is positioned on anterior portion of the vest and configured to receive a first end of a support strap;
      a posterior pair of sagittally mirrored anchor points is positioned on a posterior portion of the vest and configured to receive the first end of the support strap;
      a distal pair of sagittally mirrored anchor points is positioned on a distal portion of the pair of the sleeves of the vest and configured to receive a second end of the support strap;
   the support strap, wherein
      the first end of the support strap attaches to one of the anchor points in one of the anterior and posterior pairs of sagittally mirrored anchor points;
      the second end of the support strap attaches to one of the anchor points in the distal pair of sagitally mirrored anchor points;
      a path of the support strap transverses a sagittal plane; and
      the path of the support strap configured to spiral around an arm.

2. The system of claim 1, wherein a direction of rotational resistance in the arm is adjusted by attaching the first end of the support strap to one of the anchor points in one of the front and back pairs of sagitally mirrored anchor points.

3. The system of claim 1, further comprising a tensioning mechanism.

4. The system of claim 3, further comprising an inelastic cable running a length of the support strap.

5. The system of claim 4, wherein abduction and rotation of the arm is limited by adjusting the tensioning mechanism.

6. The system of claim 3, further comprising a strongly elastic cable running a length of the support strap.

7. The system of claim 6, wherein abduction resistance and rotational resistance of the arm is adjusted using the tensioning mechanism.

8. The system of claim 1, wherein the system comprises a plurality of the support straps.

9. A method of supporting a shoulder comprising:
   providing a vest with a pair of sleeves configured to cover an upper portion of a torso, shoulders, and at least a portion of upper arms, wherein
      an anterior pair of sagittally mirrored anchor points is positioned on a anterior portion of the vest and configured to receive a first end of a support strap;
      a posterior pair of sagittally mirrored anchor points is positioned on a posterior portion of the vest and configured to receive the first end of the support strap;
      a distal pair of sagitally mirrored anchor points is positioned on a distal portion of the pair of sleeves of the vest and configured to receive a second end of the support strap;
   putting the vest onto a wearer;
   providing the support strap;
   attaching the support strap to the vest, wherein
      the first end of the support strap attaches to one of the anchor points in one of the anterior and posterior pairs of sagittally mirrored anchor points;
      the second end of the support strap attaches to one of the anchor points in the distal pair of sagittally mirrored anchor points;
      a path of the support strap transverses a sagittal plane; and
      a path of the support strap configured to spiral around an arm.

10. The method of claim 9, wherein a direction of rotational resistance in the arm is adjusted by attaching the first end of the support strap to one of the anchor points in one of the front and back pairs of sagittally mirrored anchor points.

11. The method of claim 9, wherein the support strap further comprises a tensioning mechanism.

12. The method of claim 11, wherein the support strap further comprises an inelastic cable running a length of the support strap.

13. The method of claim 12, wherein abduction and rotation of the arm is limited by adjusting the tensioning mechanism.

14. The method of claim 11, wherein the support strap further comprises a strongly elastic cable running a length of the support strap.

15. The method of claim 14, wherein abduction resistance and rotational resistance of the arm is adjusted using the tensioning mechanism.

16. The method of claim 9, wherein a plurality of the support straps are provided and attached to the vest.

17. A shoulder support system comprising:
   a vest with a pair of sleeves configured to cover an upper portion of a torso, shoulders, and at least a portion of upper arms, wherein
      an anterior pair of sagittally mirrored anchor points is positioned on a anterior portion of the vest and configured to receive a first end of a support strap;
      a posterior pair of sagittally mirrored anchor points is positioned on a posterior portion of the vest and configured to receive the first end of the support strap;

a distal pair of sagitally mirrored anchor points is positioned on a distal portion of the pair of sleeves of the vest and configured to receive a second end of the support strap;

the support strap, wherein
the first end of the support strap attaches to one of the anchor points in one of the anterior and posterior pairs of sagitally mirrored anchor points;
the second end of the support strap attaches to one of the anchor points in the distal pair of sagitally mirrored anchor points;
a tensioning mechanism is positioned on the support strap and configured to adjust a length of a cable, the cable running a length of the support strap;
a path of the support strap transverses a sagittal plane; and
the path of the support strap configured to spiral around an arm.

18. The system of claim 17, wherein the cable is one of inelastic and strongly elastic.

\* \* \* \* \*